(12) United States Patent
Mann et al.

(10) Patent No.: US 6,242,173 B1
(45) Date of Patent: Jun. 5, 2001

(54) IMMUNOASSAYS FOR CATALYTICALLY-ACTIVE, SERINE PROTEASES

(75) Inventors: Kenneth G. Mann, Shelburne, VT (US); Brady Williams, St. Paul, MN (US); Russell P. Tracy, Essex Junction, VT (US)

(73) Assignee: University of Vermont and State Agriculatural College, Burlington, VT (US)

( * ) Notice: Subject to any disclaimer, the term of this patent is extended or adjusted under 35 U.S.C. 154(b) by 0 days.

(21) Appl. No.: 07/833,646

(22) Filed: Feb. 7, 1992

Related U.S. Application Data

(63) Continuation of application No. 07/252,506, filed on Sep. 30, 1988, now abandoned.

(51) Int. Cl.[7] .............................. C12Q 1/00; G01N 33/48; G01N 33/00; A61K 38/00
(52) U.S. Cl. .................................. 435/4; 435/7.1; 435/13; 435/28; 436/501; 436/536; 436/63; 436/86; 436/124; 530/300
(58) Field of Search .............................. 435/4, 6, 7.1, 13, 435/28, 288; 436/501, 528, 536, 63, 86, 124, 800, 824; 530/300, 802

(56) References Cited

U.S. PATENT DOCUMENTS

| | | | |
|---|---|---|---|
| 4,276,375 | 6/1981 | Claeson et al. | 435/13 |
| 4,318,904 | 3/1982 | Shaw et al. | 424/177 |
| 4,480,030 | 10/1984 | Svendsen | 435/13 |
| 4,518,528 | * 5/1985 | Rasnick | 260/112.5 R |
| 4,568,636 | 2/1986 | Svendsen | 435/13 |
| 4,582,821 | 4/1986 | Kettner et al. | 514/18 |
| 4,636,492 | 1/1987 | Kettner et al. | 514/18 |
| 4,713,369 | 12/1987 | Stuber | 514/18 |
| 4,753,875 | 6/1988 | Ryan | 435/7 |

FOREIGN PATENT DOCUMENTS 0 038 935   11/1981  (EP).

OTHER PUBLICATIONS

Bock, Paul E., Chemical Abstracts, Sep. 1988, vol. 109, No. 11, 12, abstract 88790K, p. 321.
Krishnaswamy et al., "Prothrombinase Complex Assembly," *J. Biol. Chem.*, 263:3823–3834 (1988).
Krishnaswamy et al., "The Binding of Activated Protein C to Factors V and Va," *J. Biol. Chem.*, 261(21):9684–9693 (1986).
Kourteva et al., "Assay for Enzyme Inhibition: Detection of Natural Inhibitors of Trypsin and Chymotrypsin," *Analytical Biochem.*, 162:345–349 (1987).
Tans et al., "Studies of the effect of serine protease inhibitors on activated contact factors," *Eur. J. Biochem.*, 164:637–642 (1987).

(List continued on next page.)

Primary Examiner—Ardin H. Marschel
(74) Attorney, Agent, or Firm—Lahive & Cockfield, LLP; Giulio A. DeConti, Jr.

(57) ABSTRACT

Methods for detecting and/or quantifying catalytically-active, serine proteases in a biological fluid are disclosed. The methods are useful for measuring the active enzymes of the coagulation/fibrinolytic system and evaluating the system or components of the system as indicative of thrombosis-related disorders. The methods involve the combined use of halomethyl ketone probes having broad specificity for catalytically-active serine proteases and immunological reagents specific for serine proteases of particular types. The halomethyl ketone probes are active site specific; they are only incorporated into catalytically-active serine proteases. An antibody is used to provide specificity for the particular type of serine protease. By the combined active-site-specificity of the halomethyl ketone probes and the type-specificity of the antibody, the catalytically-active fraction of a particular serine protease is determined.

36 Claims, 2 Drawing Sheets

{A}  AVIDIN
Ƴ    ANTI-COAGULATION FACTOR
ᴬₑ   PEROXIDASE CONJUGATED ANTIBODY
⊂⊃ᴮ  COAGULATION FACTOR – BCPPACK

▽    COAGULATION FACTOR
ᴱ└ᴮ  BIOTINYLATED PEROXIDASE
⊢ᴮ   BCPPACK

ASSAY FORMATS

OTHER PUBLICATIONS

Kettner and Shaw, "Inactivation of Trypsin–Like Enzymes with Peptides of Arginine Chloromethyl Ketone," *Meth. Enzymol.,* 80:826–842 (1981).

Neshein et al., "Cofactor Dependence of Factor Xa Incorporation into the Prothrombinase Complex," *J.Biol. Chem.,* 256(13):6537–6540 (1981).

Kettner and Shaw, "D–PHE–PRO–ARGCH$_2$Cl–A Selective Affinity Label from Thrombin," *Thrombosis Res.,* 14:969–973 (1979).

Plotkin and Coleman, *Bio/Technology,* 6:644 (1988).

Rauber et al. (1986) Biochemical J., vol. 239, pp. 633–640.*

* cited by examiner

FIG. 1 ASSAY FORMATS

US 6,242,173 B1

IMMUNOASSAYS FOR CATALYTICALLY-ACTIVE, SERINE PROTEASES

RELATED APPLICATIONS

This application is a continuation of U.S. Ser. No. 07/252,506, filed on Sep. 30, 1988, now abandoned, the contents of which are incorporated herein by reference.

BACKGROUND

Thrombosis and thrombolysis are maintained in delicate balance by a series of high regulated enzymatic reactions. The component enzymes are are largely serine proteases which are produced as needed from zymogens, inactive forms of the enzymes which circulate in the blood at relatively high concentrations. It has become increasingly clear that the active forms of the pro- and anti-coagulant enzymes may be useful for evaluating patients afflicted with or at risk for thrombosis-related disorders.

For example, epidemiologic studies have demonstrated that elevated levels of fibrinogen and factor VII are associated with an increased risk of coronary artery disease and stroke. Some investigators have differentiated between activated and unactivated factor VII and find that the level of activated factor VII is the better risk indicator. In addition, there is evidence which suggests that the subset of the population that develops atherosclerosis may have a form of thrombotic diathesis which might manifest itself in the form of a chronic increase in activation of the coagulation/fibrinolytic system. Thrombotic manifestations of atherosclerotic disease such as stroke and myocardial infarction represent the major causes of mortality in the western industrialized world.

Identifying and evaluating patients at risk for thrombotic disorders will require accurate measurement of plasma levels of active pro- and anti-coagulant factors of the coagulation/fibrinolytic system. The need for this capability will grow in years to come. Heart disease, stroke and the many other thrombosis-related disorders occur most frequently in the older segment of the population. With the rapid growth of the older cohort of our population, the capability to monitor the activation state of coagulation/fibrinolytic system will be of increasing clinical utility.

SUMMARY OF THE INVENTION

This invention pertains to assays for detecting and/or quantifying catalytically-active, serine proteases in a biological fluid. The methods are useful for measuring the active enzymes of the coagulation/fibrinolytic system and evaluating the system or components of the system as indicative of thrombosis-related disorders. The methods involve the combined use of halomethyl ketone probes having broad specificity for catalytically-active serine proteases and immunological reagents specific for serine proteases of particular types. The halomethyl ketone probes are active site specific; they are only incorporated into catalytically-active serine proteases. An antibody is used to provide specificity for the particular type of serine protease. By the combined active-site-specificity of the halomethyl ketone probes and the type-specificity of the antibody, the catalytically-active fraction of a particular serine protease is determined.

In the assays of this invention, the halomethyl ketone probe is incubated with a sample of biological fluid so that it is incorporated generally into catalytically-active serine proteases in the sample. Depending on the format of the assay, the halomethyl ketone probe is coupled to a detectable label, to a group which can be labeled or to a group that provides a secondary recognition site for capture onto a solid phase. Thus, incorporation of the halomethyl ketone labels the active serine proteases either for detection or for separation. A mono-specific antibody is incubated with the biological fluid to selectively bind serine proteases of the type to be determined. In formats of the assay where the halomethyl ketone provides a label for detection, the antibody can be linked to a solid phase to effect type-specific separation of the serine proteases to be determined. In formats of the assay where the halomethyl ketone provides a secondary recognition site for separation, the antibody is used to type-specifically label the serine protease for detection.

The invention also pertains to a method of separating catalytically-active serine proteases from a biological fluid. The method involves the incorporation of a biotinylated halomethyl ketone into the active site of serine proteases and the adsorption of the serine proteases onto an avidin-coated solid phase to effect separation.

DETAILED DESCRIPTION OF THE INVENTION

Figure 1:
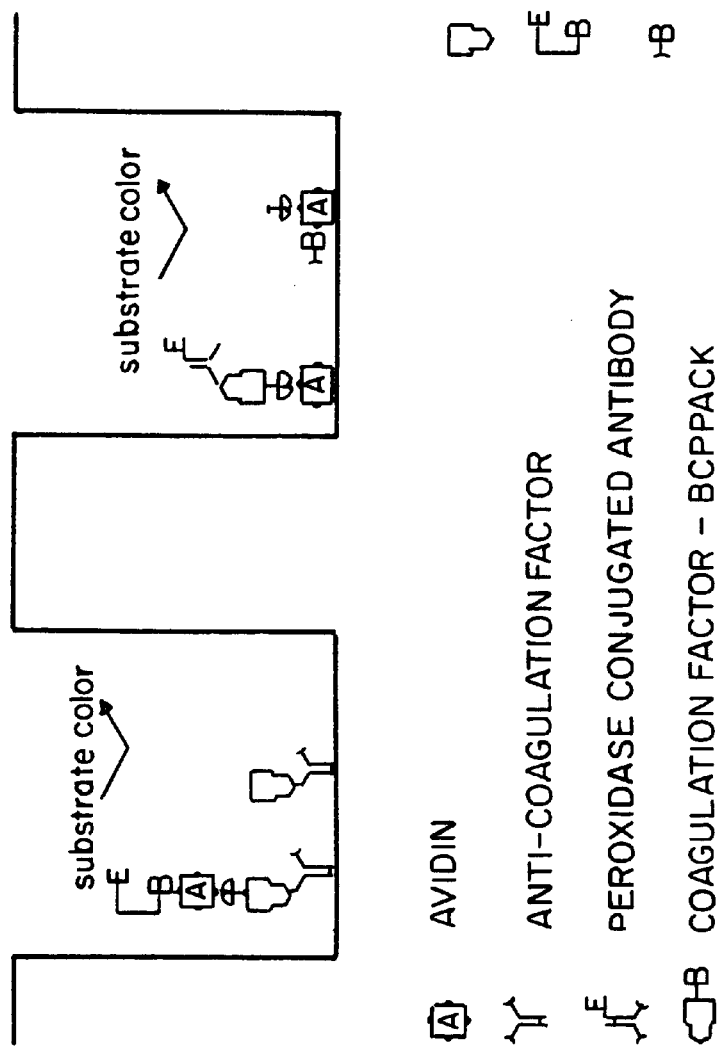
FIG. 1 is a schematic depiction of two formats for the immunoassays of this invention.

The assays of this invention can be used to detect and/or quantify catalytically active serine proteases involved in thrombosis and thrombolysis. These include tissue plasminogen activator, urokinase, factor VIIa, factor IIa, factor IXa, factor Xa, plasmin, and activated protein C. The assays provide accurate measurement of levels of the catalytically active forms of the enzymes. The assays can be performed as heterogenous or homogenous assays in different formats. Preferred embodiments, as described below, are solid phase assays. In addition to the detection systems described below, halomethyl ketone probe-antibody communication systems (e.g., energy transfer fluorescence) can be used.

In one format of the assays, a labeled halomethyl ketone is used to directly label catalytically-active serine proteases in a sample of biological fluid and an antibody specific for the serine protease of a particular type is employed to selectively separate the serine protease. A halomethyl ketone linked to a detectable label (e.g., an enzyme, fluorophore or radioisotope as described in greater detail below) is incubated with the biological fluid under conditions which permit the active site specific, labeled halomethyl ketone to be incorporated covalently into the serine proteases in the biological fluid. After the this first incubation, the biological fluid is incubated with a solid phase immunoadsorbent which contains an antibody specific for a serine protease of the particular type to be determined (tissue plasminogen activator, factor VIIa, etc.). The incubation is conducted under conditions which allow the particular serine protease to be selectively adsorbed to the immunoadsorbent (by completing with antibody thereon). After the incubation, the immunoadsorbent and the biological fluid are separated and amount of label associated with the immunoadsorbent is determined. The amount of label associated with the immunoadsorbant is directly proportional to the amount of the serine protease in the biological fluid.

In a variation of this format, the halomethyl ketone can be linked to a moiety such as biotin which serves as a secondary recognition site for attachment of a detectable label after the halomethyl ketone has been incorporated into the serine proteases. Following selective adsorption of the serine protease onto the antibody-coated immunoadsorbant, a complex of avidin-biotin-label (e.g., enzyme) can be attached to the biotinylated halomethyl ketone. The amount of label associated with the solid phase is then determined.

In another format of the assay, the halomethyl ketone is used to incorporate a secondary recognition site into serine proteases which can then be exploited to adsorb the catalytically-active fraction of serine proteases onto a solid phase. In this format also biotin can be used to provide the secondary recognition site for attachment of the serine proteases onto an avidin coated solid phase. Accordingly, the biotinylated halomethyl ketone is incubated with the biological fluid under conditions sufficient for incorporation into the catalytically active site of the serine proteases. Thereafter, the biological fluid is incubated with an solid phase adsorbant coated with avidin. The incubation is performed under conditions which allow the serine proteases which have incorporated the biotinylated halomethyl ketone (i.e. the catalytically-active serine proteases now deactivated by the incorporated halomethyl ketone) to be adsorbed to the avidin-coated adsorbant. After the incubation, the adsorbant and the biological fluid are separated, then the adsorbant is incubated with a labeled antibody specific for the particular type of serine protease to be assayed. As in the prior format, the amount of label associated with the adsorbant is determined as indicative of the amount of the catalytically-active serine protease in the biological fluid.

The two different assay formats described above are illustrated in their preferred embodiments in FIG. 1. The assays depicted are enzyme-based colorimetric assays but as described above they may be radioassays or fluorescent assays. In the assay format depicted in the left side of the figure, the coagulation factor (a serine protease) in a sample of biological fluid is allowed to react with the biotinylated chloromethyl ketone-biotinyl-$\epsilon$-aminocaproyl-D-phenylalanyl-L-prolyl-L-arginine chloromethyl ketone (BCPPACK). The coagulation factor-BCPPACK complex is immobilized specifically onto a solid phase coated with anti-coagulation factor (e.g., antibody). The immobilized coagulation factor is then detected or quantified with a biotinylated peroxidase which is linked to the coagulation factor-BCPPACK complex via avidin. In the assay format depicted in the right side of the figure, the coagulation factor-BCPPACK complex is immobilized onto an avidin coated, rather than anti-coagulation factor coated, solid phase. The immobilized coagulation factor is then detected or quantified by means of peroxidase conjugated antibody.

The assays of this invention can be performed on samples of essentially any biological fluid. Typically, the assays are performed on blood or components of blood such as plasma or serum, but other fluid such as lymph, digestive juices or urine can be used. The biological fluid may also be a sample of a liquid medium in which animal or microbial cells have been cultured. The biological fluid or sample for testing can be directly collected in or added to a tube containing halomethyl ketone.

The preferred halomethyl ketones for use in the assays of this invention are chloromethyl ketones, particularly peptidyl chloromethyl ketones which are specific for the $S_1$ subsite of the active site of serine proteases. The preferred chloromethyl ketones can be represented generally by the formula:

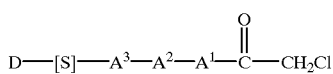

In this formula, $A^1$, $A^2$, and $A^3$ signify an amino acid or amino acid analogue. $A^1$ is an amino acid or amino acid analogue which provides the preferred specificity for the $S_1$ subsite of the catalytic site of serine proteases. $A^1$ can be any amino acid which confers the appropriate subsite specificity. For trypsin-like enzymes, $A_1$ can be arginine (R), lysine (K), and homoarginine (hR). For blood clotting and thrombolytic enzymes, preferably, $A^1$ is arginine. $A^2$ and $A^3$ can be any amino acid or analogue. $A^3$ is preferably an aromatic amino acid such as tyrosine (Y) and phenylalanine (F).

Depending on the format of the assay as described above D represents a chemical group which can be selectively recognized and thus provides either for detection or for separation of serine proteases which have taken up the tripeptidyl chloromethyl ketone. For example, D can be label, such as a fluorophore, radioisotope or enzyme which is directly linked to the tripeptidyl chloromethyl ketone (optionally through a spacer S as described below). Alternatively, D can be a group, such as biotin, which can be linked to a detectable label after the chloromethyl ketone is incorporated into the active site of the serine protease. A biotinylated chloromethyl ketone, for example, can be labeled for detection with an avidin-biotin-enzyme complex. D can also be a group which provides a secondary recognition site for capture onto a solid phase, e.g., an avidin-coated solid phase, as described in the second format of the assay above.

S signifies a spacer group which may be necessary to link D to the tripeptidyl chloromethyl ketone. For biotin, a spacer has been found necessary to make it available for avidin binding when incorporated into the serine proteases. A preferred spacer group for linking biotin to the chloromethyl ketone is represented by the formula:

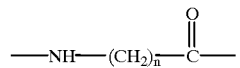

wherein n is 3–8. The preferred linker is $\epsilon$-amino caproic acid (n=5 in the above formula.)

Especially preferred biotinylated chloromethyl ketones for use in the assay of this invention are the following:

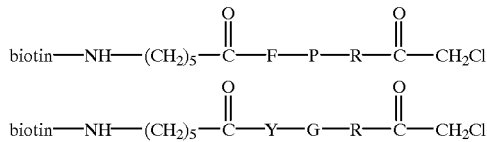

In the assays of this invention, antibodies provide type-specificity for the serine proteases. The antibodies can be used to selectively identify and label a particular type of serine protease or to selectively separate the serine protease. Antibodies specific for serine proteases can be polyclonal or monoclonal and can be obtained commercially or made by standard techniques.

In formats of the assays where a labeled antibody is required for type specific labeling of serine proteases the labels can be enzymes, fluorophores or radioisotopes. Preferred enzymes are peroxidases (for example, horseradish peroxidase). The activity of a peroxidase can be determined colorimetrically by employing a chromogenic substrate such as O-phenylenediamine-2HCl. Suitable fluorophores for labeling antibody include dansyl, fluoresceinyl rhodaminyl groups and europium. Suitable radioisotopes are the gamma emitters $^{131}$I and $^{125}$I. These various types of labels can be attached to the antibody by techniques well known in the art. For example, an enzyme can be linked to an antibody by an avidin-biotin linkage according to standard procedures. Fluorophores can be chemically coupled to antibodies. Radioisotopes can be linked either directly or through a alkylating or chelating agent.

For selective separation of serine proteases, antibody can be immobilized onto a solid phase to provide an immunoadsorbent specific for a particular type of serine protease. Many types of solid-phases may be employed. Well-known solid phases include beads made from glass, latex, polystyrene, polypropylene, dextran, and other materials; tubes formed from or coated with such materials, microtiter plate wells coated with such materials, etc. A "solid phase" can also be small particles suspended in a liquid medium, e.g., lipid particles (liposomes). Those skilled in the art will know many other suitable solid-phases and methods for immobilizing antibodies thereon, or will be able to ascertain such using no more than routine experimentation.

The antibody can be either covalently or non-covalently coupled to the solid-phase by techniques such as covalent bonding via an amide or ester linkage or adsorption.

In one of the formats of the assay described above, an avidin-coated immunoadsorbant is used to capture serine proteases which have incorporated a biotinylated chloromethyl ketone. Avidin-coated immunoadsorbants can be prepared in the same manner as antibody immunoadsorbants.

In each of the various embodiments of the solid phase assays described, the amount of a particular serine protease in the biological fluid is determined by measuring the amount of label associated with the immunoadsorbant. The amount of label associated with the solid phase is directly proportional to the amount of serine protease in the biological fluid. (In some formats of the assays, the amount of the label which remains soluble can be measured (instead of the label associated with the solid phase); in this case the amount of soluble label is indirectly proportional to the amount of serine protease in the biological fluid).

The label associated with the solid phase is measured by standard techniques. If the label is a radioactive gamma emitter, the label is measured directly by a gamma counter, for example; if the label is a fluorescent compound it is measured by a fluorimeter. In the case of an enzyme label, the amount of label is measured by colorimetric methods employing a chromogenic substrate for the enzyme.

The measured amount of label detected is then compared to a pre-established quantitative relationship between the amount of label and the amount of the serine protease. The quantitative relationship can be determined by performing the assay with standards—liquid samples containing known amounts of the particular serine protease. For several samples containing different amounts of the serine protease, the assay is conducted and the amount of label bound to the immunoadsorbent is determined; a curve is constructed defining the quantitative relationship between the amount of label and the amount of the particular serine protease. By reference to the curve, the amount of the particular serine protease (in the sample containing an unknown amount) can be determined by the amount of label detected.

The reagents for performing the assays of this invention may be assembled in assay kits. The kits can be designed for the various formats of the assays. A kit for performance of an assay of the first format described above contains (in separate containers) a labeled halo(chloro)methyl ketone specific for catalytically active serine proteases and an immunoadsorbant containing antibody specific for the particular type of serine protease to be determined. For the variation of this format, in which a biotinylated chloromethyl ketone is used, a kit contains a biotinylated halomethyl ketone, an avidin-bound label and an immunoadsorbent containing antibody specific for the particular type of serine protease to be determined. For the second format of the assay as described above, a kit contains a biotinylated halomethyl ketone, an avidin-coated adsorbent and a labeled antibody specific for the particular type of serine protease to be determined. Other components of the kits can be serine protease standards, a positive control (for example, a biological fluid containing a known amount of serine protease), and, where an enzyme label is used, a chromogenic substrate for the enzyme (for example, for a peroxidase such as horse radish peroxidase the substrate O-phenylenediamine-2HCl).

The assays of this invention have various clinical utilities, including the evaluation of (1) thrombosis risk, (2) thrombolytic therapy, and (3) the continuity of the hemostatic system. To evaluate the risk of thrombosis, the assays can be used to evaluate the nature and quantity of activated enzymes of the coagulation system in the blood of patients. During thrombolytic therapy, significant amounts of thrombolytic agents are infused intravenously. For example, tissue plasminogen activator is given to bring about plasminogen activation and lysis of a blood clot. The extent and rate of lysis is directly dependent upon (among other things) the level of active tissue plasminogen activator in circulation and potentially the level of other agents such as plasmin and the coagulation enzymes. By incorporation of a halomethylketone in the blood collection system the reactions ongoing in the blood sample can be stopped quickly and the extent of enzyme labeling tissue plasminogen activator and plasmin can be assessed.

The evaluation of hemostatic risk involves a series of assays which are aimed at identifying and interpreting discontinuities or aberrations in the zymogen-enzyme conversion reactions in the blood coagulation pathway to generate thrombin, and ultimately the fibrin clot. Clotting can be initiated in a plasma sample, for example, through the contact pathway or through the extrinsic pathway of coagulation. After a brief interval, a halomethylketone is added to the plasma reaction system. This labels all enzymes which have been generated from zymogens during the activation process. Subsequent screening for the nature of the enzymes activated identifies the source of discontinuity or aberration in the coagulation system.

The biotinylated chloromethyl ketones of this invention can also be used to separate catalytically active serine proteases from a biological fluid. For this purpose, a biotinylated chloromethyl ketone is incubated with a biological fluid under conditions sufficient for the biotinylated chloromethyl ketone to be incorporated into the site. The biological fluid is then contacted with a solid phase adsorbent containing avidin under conditions which allow serine proteases which have incorporated the biotinylated chloromethyl ketone to be adsorbed to the adsorbent. The biological fluid and the adsorbent are then separated.

The invention is further illustrated by the following examples.

EXAMPLES

Example I

Preparation of Biotinylated Chloromethyl Ketones
Biotinyl-D-phenylalanyl-L-prolyl-L-arginine Chloromethyl Ketone (Biotinyl-PPACK)

PPACK.2HCl [Boeringer/Calbiochem] (16.2 mg, 30.0 µmoles) and KHCO$_3$ (6.0 mg, 60. µmoles) were dissolved in water (0.50 mL) and immediately reacted with Biotin N-hydroxysuccinimide ester (Sigma) (10.2 mg, 30 µmoles) in DMF (0.50 mL). After 10 minutes at 22° C., the reaction was acidified with 1.0M HCl (0.30 mL). The crude product was chromatographed on SEPHADEX LH-20 gel (20×cm) using methanol as eluant. Elution was followed by A$_{254}$ and Sakaguchi stain. Fractions above baseline were dried individually and dissolved in 1.0 mM HCl (1 mL each). The solutions were tested for ability to inhibit the hydrolysis of S2222 by bovine Xa and for enhancement of the fluorescence of fluorescein-avidin (Sigma). Those samples testing positive for both were lyophilized. Thin layer chromatographic analysis (Bakerflex silica eluted with chloroform:methanol 3:1) indicated the samples were homogenous and identical (R$_f$=0.34). Combined yield 18.6 mg (87%). The solid was dissolved in 10 mM HCl (2 mL) and stored frozen at −20° C. Final concentration is 13 mM.

Biotinyl-ε-aminocaproyl-PPACK (BC-PPACK)

PPACK.2HCl (10.5 mg, 20 µmole) and KHCO$_3$ (3.0 mg, 30 µmole) were dissolved in water (0.40 mL) and immediately added to N-hydroxysuccinyl biotinyl-ε-aminocaproate (Sigma) (9.1 mg, 20 µmoles) in DMF (0.40 mL). Purified and characterized as with biotinyl-PPACK (above); R$_f$=0.41, yield=9.2 mg (56%). Final solution (in 10 mM HCl) was 5.6 mM.

N-tBOC-(O-benzyl)-L-tyrosinyl-glycyl-L-arginine chloromethyl ketone

N-tBOC-(O-benzyl)-L-tyrosine (Sigma) (7.43 g, 20 mmole) and N-hydrodroxysuccinimide (Aldrich) (2.50 g, 22 mmoles) were dissolved in dimethyoxyethal (DME) (20 ml) cooled to 0° C. and treated with dicyclohexylcarbodiimide, (Aldrich) (4.54 g, 22 mmoles). After 1 hour at 0° C. and 2 hours at 22° C., ethyl acetate (250 mL) was added to the solidified reaction mixture and the slurry was filtered. The residue was resuspended in ethyl acetate (100 mL) and filtered twice more. The combined filtrates were evaporated in vacuo to a thick oil which was recrystalized from hot isopropanol. Yield of the BOC-O-Bz-Tyr-ONSu was 7.68 g (82%).

BOC-O-Bz-Tyr-ONSu (4.69 g, 10 mmoles) was suspended in DME (10 mL) and treated with a solution of glycine (0.75 g, 10 mmoles) and KHCO$_3$ (1.00 g, 10 mmoles) in water (30 mL). The reaction foamed vigorously at first. After 1 hour stirring at room temperature, the mixture had cleared and no additional evolution was observed. The reaction was acidified carefully to pH=3 with cold 1M H$_2$SO$_4$ and diluted with water (100 mL). The product was extracted with ethyl acetate (2×50 mL) and the combined extracts were washed with water (3×50 mL) and saturated NaCl (50 mL), dried over anhydrous sodium sulfate and evaporated to a solid. The solid was recrystalized from chloroform-hexane. Yield of BOC-(O-Bz)-Tyr-Gly was 3.20 g (75%).

BOC-(O-Bz)-Tyr-Gly (2.15 g, 5.0 mmole) was dissolved in THF (5 mL) at −20° C. and treated with 4-methylmorpholine (Aldrich) (0.564 mL, 5.0 mmole) and isobutyl chloroformate (Aldrich) (0.660 mL, 5.0 mmole). After 30 minutes at −20° C., the reaction mixture was treated with a cold (−20° C.) solution of ε-nitro-L-arginine chloromethyl ketone HCl (1.44 mg, 5.0 mmole) in 5.0 mL DMF followed immediately be 4-methylmorpholine (0.564 mL, 5.0 mmole). The reaction was allowed to run at −20° C. for 2 hours and then slowly warmed to 22° C. over an additional 2 hours. Ethyl acetate (50 mL) was added and the solution extracted with 1M H$_2$SO$_4$ (25 mL), water (3×) and brine, dried over anhydrous sodium sulfate and evaporated to an oil. Recrystallization from chloroform-ether gave homogeneous product. Yield of BOC-(O-Bz)-Tyr-Gly-(ε-NO$_2$)-Arg-CK was 0.93 g (28%).

Biotinyl-ε-aminocaproyl-L-tyrosylglycyl-L-arginine chloromethyl ketone (BC-YGR-CK)

BOC-(O-Bz)-Tyr-Gly-(ε-NO$_2$)-Arg-CK (132 mg, 0.20 mmole) was dissolved in saturated HCl/methanol (10 mL) and stirred 10 minutes. The solvent was removed in vacuo and replaced with a second aliquot of the HCl/methanol (10 mL). After 20 minutes, the solvent was removed and ether (50 mL) was added. The solvent was decanted from the precipitated product and the solid was pumped at high vacuum overnight over KOH pellets.

The residue was dissolved in DMF (1.0 mL) and added to a solution of N-hydroxysuccinyl biotinyl-ε-aminocaproate (91 mg, 0.20 mmoles). To this was added KHCO$_2$ (40 mg, 0.40 mmole) in water (0.50 mL). The reaction was allowed to run at 22° C. for 30 minutes then treated with methanolic HCl (5 mL) and ether (50 mL). Two phases were formed. The ether (upper) phase was removed and the lower phase was applied directly to a SEPHADEX LH-20 column (1×20 cm) and eluted with methanol. A single peak was observed by A$_{280}$. This was homogeneous by thin layer chromatography (5:1 chloroform:methanol, R$_f$=0.21). Product was precipitated with ether and collected by filtration. Yield was 69 mg (35%) of the blocked, biotinylated peptide [BC-(O-Bz)-Tyr-Gly-(ε-NO$_2$)-Arg-CK].

The above product (65 mg, 66 µmole) was reacted with liquid hydrogen fluoride in a Biosearch HF cleavage reactor. After 30 minutes, the HF was evaporated under vacuum and the dark residue was held under water pump vacuum overnigtht over KOH. The residue was treated with 1.0 mM HCl and filtered. The filtrate was lyophilized to an off-white solid which was taken up in methanol (0.5 mL) and chromatographed on SEPHADEX LH-20 (1×20 cm) in methanol. Elution gave a single major peak (A$_{280}$) which was Sakaguchi positive and inhibited the reaction of bovine factor Xa with S2222. The pooled peak was evaporated to a solid which was taken up in 1 mM HCl and lyophilized. Yield was 50.2 mg (87%). The solid was taken up in 10 mM HCl and frozen. Final concentration was 13 mM.

Preparation of Biotinylated Enzymes

The purified enzymes were diluted to approximately 0.5 mg/mL in Hepes (20 mM)/NaCl (150 mM) pH=7.4 (Factor VIIa preparations were at 0.1 mg/mL. Human factor VII was converted to VIIa by incubation for 1 hour with a 0.2% (w/w) aliquot of human Xa). Biotinylated peptide chloromethyl ketone was added in 0.5 molar equivalent aliquots and allowed to react for five to ten minutes at 37° C. For those enzymes for which a direct chromogenic substrate is available, the reaction mixture was assayed to determine degree of reaction. The coupled assay for factor VIIa could not be used due to the interference of residual chloromethyl ketone Xa produced in the assay. All assayed proteins were completely inhibited by from 1.5 to 2.0 equivalents of each of the preparations. One additional equivalent of chloromethyl ketone was added to ensure completion, and the reaction was allowed to proceed for an hour past completion. A typical reactivity curve is shown in Table I.

TABLE I

Reaction of Human Xa with BC-PPACK

| equivalents added | relative activity (vs. S2222) |
| --- | --- |
| 0 | 1.00 |
| 0.46 | 0.62 |
| 0.92 | 0.13 |
| 1.38 | 0.01 |
| 1.84 | 0.00 |
| 2.76 | 0.00 |

For factor VIIa, 5 equivalents of inhibitor were used. To remove residual inhibitor, the proteins were chromatographed on SEPHADEX G-25 (1×20 cm) in Hepes/saline, followed by $A_{280}$.

Screening of Protein/BC-PPACK Reactions

Samples of purified enzymes, zymogens, or enzyme-zymogen mixtures were treated with BC-PPACK as follows: 10–30 μg samples of protein at 0.5 mg/mL in Hepes (20 mM)/NaCl (150 mM) pH=7.4 was reacted with 10 fold molar excess of BC-PPACK for 30 minutes, followed by a second 10 fold aliquot and overnight incubation at room temperature. Samples were then reduced with 2-mercaptoethanol and prepared for PAGE gel electrophoresis either on 12×12 cm or PhastGel systems. After electrophoresis, the gels were blotted to nitrocellulose using tris/glycine methanol transfer buffer. The nitrocellulose was then blocked with TWEEN reagent, washed with tris/glycine and reacted with avidin-biotin-peroxidase. Development with 4-chloronapthtalene visualized the biotinylated proteins.

Proteins testing positive included thrombin (hIIa), factor Xa (hXa), factor VIIa (hVIIa), tissue plasminogen activator (tTPA) (1 and 2 chain) and plasmin (hPm). No reaction was observed with hII, hVII, hX or hPg. Identical results were found with BC-YGR-CK except that the plasminogen/plasmin system was not tested. When biotinyl-PPACK without the caproyl spacer was used, none of the proteins showed a positive blot.

Reaction of Activated Human Plasma With BC-YGR-CK

Normal human plasma (200 μL) at 37° C. was activated with thromboplastin (10 μL) and $Ca^{+2}$ (4 mM). At timed intervals, 20 uL aliquots were removed and added to 2 μL aliquots of 13 mM BC-YGR-CK (final CK concentration was 1.2 μM). A clot was observed after 122 seconds. The samples were then run on PhastGel electrophoresis and blotted to nitrocellulose. Development of the blot (as above) revealed several biotinylated proteins for which the concentrations varied during the time course.

Example II
Solid-Phase Antibody Assay for Factor Xa-BCPPACK

Anti-factor Xa antibodies were absorbed into microtiter plate wells (at a concentration of 10 ug/ml in a coating buffer of 0.1M carbonate, pH 9.0). Varying amounts of factor Xa-BCPPACK was added followed with avidin-biotinylated peroxidase reagents and finally substrate (with appropriate washes).

Figure 2:
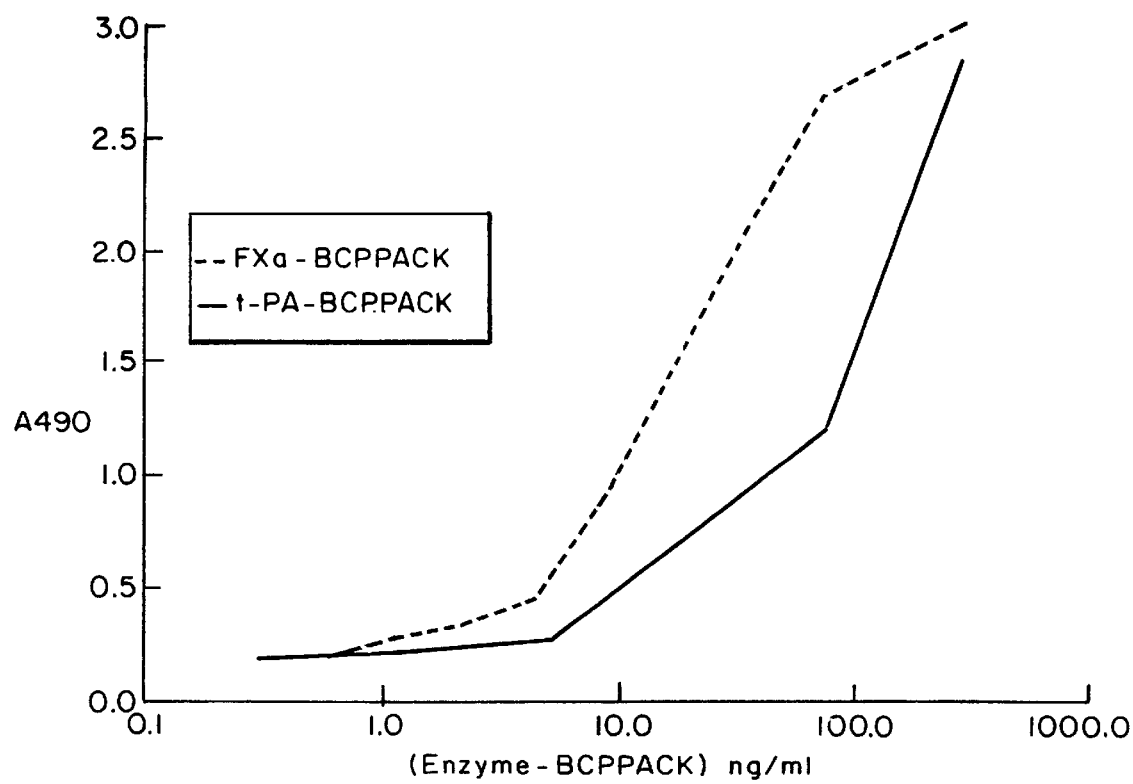
FIG. 2 shows standard curves for a solid phase antibody assay for Factor Xa-BCPPACK and tPA-BCPPACK.

A standard curve (FIG. 2) was established with sensitivity to approximately 4 mg/ml factor Xa-BCPPACK, as determined by serial dilutions. The procedure was repeated for tPA-BCPPACK (FIG. 2).

Example III
Colorimetric Active Site-Specific Immunoassay (CASSIA) for Tissue-type Plasminogen Activator (tPA)

Avidin was coated onto microtiter plate wells at 25 ug/ml, and tPA-BCPPACK was added as a serial dilution. The tPA-BCPPACK stock solution, 50 ug/ml, contained the excess BCPPACK, which had been used at approximately 1 μM. The first dilution in the assay is 1:200 or 250 ng/ml tPA-BCPPACK. This has a corresponding excess BCPPACK concentration of approximately 5 mM, or, stoichiometrically, a two-fold excess. Once the tPA-BCPPACK was bound it was followed with peroxidase-conjugated anti-tPA antibody, and substrate.

Figure 3:
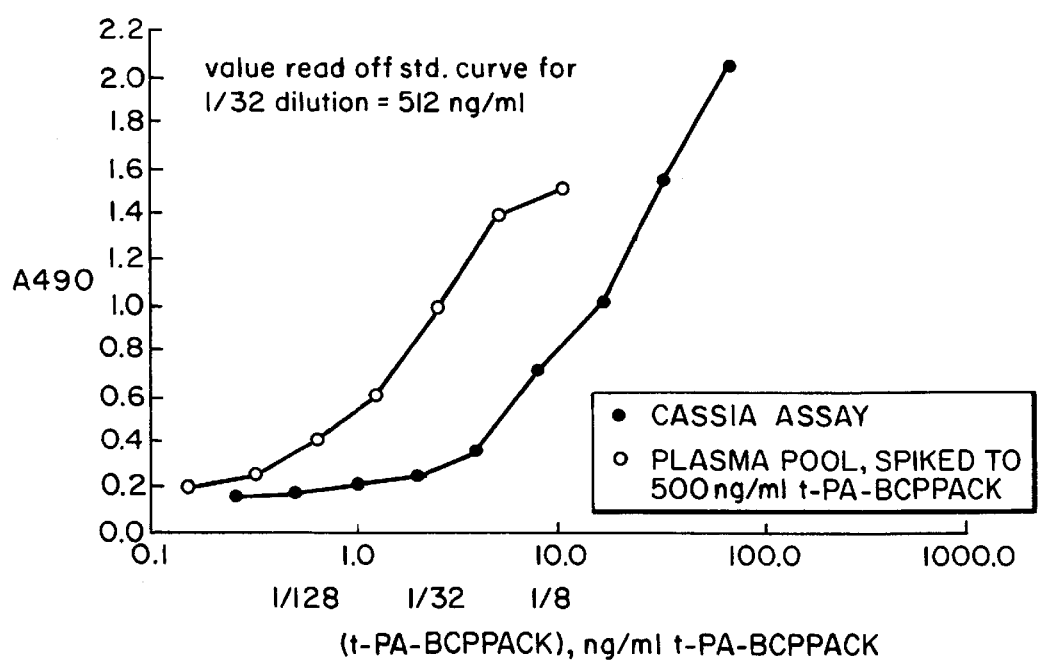
FIG. 3 shows a standard curve for a colorimetric active-site specific immunoassay for tPA.

A standard curve was established (FIG. 3), which is sensitive to approximately 2 ηg/ml tPA-BCPPACK. We also analyzed plasma which had been spiked with stock solution to a value of 500 ng/ml tPA-BCPPACK, a level achieved during thrombolytic therapy.

Example IV
Preparation of Fluorescent Chloromethyl Ketone Derivatives

Methods

Gel Electrophoresis (SDS-PAGE) was carried out on either 20×20 cm gels as described by Laemmli (Laemmli, U. K. (1970) *Nature* 227:680–685) or on a Pharmacia Phastgel system (*Phastsystem Handbook,* Pharmacia). Fluorescence spectra were obtained with a SLM 8000 photon counting fluorescence spectrophotometer or on a Perkin-Elmer Model MPF-44A. Kinetic measurements were carried out on a Cary 219 UV/visible spectrophotometer.

Except where noted, protein reactions and chromatography were carried out in Hepes (20 mM)/NaCL (150 mM) pH–7.40 (Hepes/saline). All buffers were prepared in distilled, deionized water from a Millipore "Milli-Q" system. Reagents and solvents used were reagent grade and, where indicated, were further purified by recrystalization or distillation. Fluorescent probe N-hydroxysuccinimide esters and sulfonyl chlorides were obtained from Molecular Probes, Inc. and chromogenic substrates from Helena Laboratories.

Proteins

Except as noted, all proteins were isolated from fresh frozen human plasma and were chromatographically and electrophoretically pure. Individual proteins were purified using the monoclonal antibody system described by Jenny et al. (Jenny, R., Church, W., Odegaard, B., Litwiller, R. & Mann, K. (1986) *Prep. Biochem.* 16:227–245). Prothrombin was activated by the method of Lundblad, Kingdon and Mann (Lundblad, R. L., Kingdon, H. S. & Mann, K. G. (1976) *Methods. Enzymol.* 45:156–176), factor IX by the method of Kulousek, Konigsberg and Nemerson, (1975) *FEBS Lett.* 50:382–385, factor X by reaction with Russell's viper venom X activator followed by purification on benzamidine Sepharose, and protein C by reaction with thrombin (Kisiel, W. and Davie, E. W. (1981) *Methods Enzymol. Protein C.* 80:320–332. Human factor VII generally was isolated as a mixture of factor VII and activated species (VIIa). The other zymogen preparations contained only traces of the activated forms.

Plasminogen was isolated by passing thawed, aprotinin treated plasma over lysine-Sepharose and eluting the bound plasminogen with ε-aminocaproic acid (ECAC) (Castellino, F. J. and Powell, J. R. (1980) *Methods Enzymol.* 80:365–378). A second pass over the lysine SEPHAROSE gel, followed by separation from aprotinin on SEPHAROSE gel G-100 gave plasminogen which was homogeneous when evaluated by gel electrophoresis. Plasmin was prepared from plasminogen by treatment with 1:200 (weight:weight) of urokinase in Hepes/saline. Tissue plasminogen activator (tPA) was recombinant human tPA (Genentech) and contained both single chain and two chain forms. Urokinase was a generous gift from Dr. David Stump and was two chain.

Initial reaction studies involving tissue factor used rabbit thromboplastin (Sigma). When the thrombo-plastin was found to exhibit significant proteolytic activity, purified, reconstituted tissue factor, a generous gift of Dr. Sam Rapaport, was used. In subsequent work, purified, lipid free human tissue factor, a generous gift of Dr. Tom Edgington, was used. For reconstitution, the tissue factor was precipitated from Hepes/Tween with 80% acetone. After removal of the acetone by decanting and aspiration, the protein was taken up in Hepes/saline and treated with phospholipid (75% phosphatidyl choline/25% phosphatidyl serine) (PCPS) prepared by the method of Higgins and Mann (Higgins D. L. & Mann. K. G. (1983) *J. Biol. Chem.* 258:6503–6508) and $CaCl_2$ to give 10–100 mM PCPS and 4 mM Ca(II). These preparations were assayed for tissue factor activity using the methods described below for the coupled factor VII assay.

Tissue factor was blocked with DFP by reacting the original Hepes/TWEEN solution with DFP at 10 mM final concentration for one hour, then precipitating with acetone as above. This precipitate was either reconstituted or further blocked. Similarly, tissue factor was blocked by reaction with 1.0 mM FPRck for 24 hours or with p-chloromercuribenzoate at 100 M for 2 hours. One sample was subjected to all three treatments. In each case, the specific activity of the tissue factor was decreased 10–20% by the treatment. The triply blocked sample retained roughly 55% of the original activity. Gel analysis of the tissue factor from both sources indicated a single protein with an apparent molecular weight of 45000. This value was used in subsequent calculations.

N-tBOC-(O-benzyl)-L-tryrosylglycyl-($\epsilon$-nitro)-L-arginine chloromethyl ketone N-tBOC-(O-benzyl)-L-tyrosine (Sigma) 7.43 g, 20 mmole) and N-hydroxysuccinimide [HONSu] (Aldrich) (2.50 g, 22 mmoles) were dissolved in dimethoxyethane [DME] (20 mL at 0° C. and treated with dicyclohexylcarbodiimide (Aldrich) (4.54 g, 22 mmoles). After 1 hour at 0° C. and 2 hours at 22° C., ethyl acetate (250 mL) was added to the solidified reaction mixture and the slurry was filtered. The residue was resuspended in ethyl acetate (100 mL) and filtered twice more. The combined filtrates were evaporated in vacuo to a thick oil which was recrystallized from hot isopropanol. Yield of the tBOC(-O-Bz)-Tyr-ONSu was 7.68 g (82%).

tBOC-(O-Bz)-Tyr-ONSu (4.69 g, 10 mmoles) was suspended in DME (30 mL) and treated with a solution of glycine (0.75 g, 10 mmoles) and $KHCO_3$ (1.00 g, 10 mmoles) in water (30 mL). The reaction foamed vigorously at first. After 1 hour stirring at room temperature, the mixture had cleared and no additional ebullition was observed. The reaction was acidified carefully to pH=3 with cold 1 M $H_2SO_4$ and diluted with water (100 mL). The product was extracted with ethyl acetate (2×50 mL) and the combined extracts were washed with water (3×50 mL) and saturated NaCl (50 mL), dried over anhydrous sodium sulfate and evaporated to a solid. The solid was recrystallized from chloroform-hexane. Yield of tBOC-(O-Bz)-Try-Gly was 3.20 g (75%).

tBOC-(O-Bz)-Try-Gly (2.15 g, 5.0 mmole) was dissolved in tetrahydrofuran [THF] (5 mL) at −20° C. and treated with 4-methylmorpholine (Aldrich) (0.564 mL, 5.0 mmole) and isobutyl chloroformate (Aldrich) 0.660 mL, 5.0 mmole). After 30 minutes at −20° C., the reaction mixture was treated with a cold (−20° C.) solution of -nitro-L-arginine chloromethyl ketone HCl (1.44 mg, 5.0 mmole) in 5.0 mL dimethylformamide [DMF] followed immediately by 4-methylmorpholine (0.564 mL, 5.0 mmole). The reaction was allowed to run at 20° C. for 2 hours and then slowly warmed to 22° C. over an additional 2 hours. Ethyl acetate (50 mL) was added and the solution extracted with 1 M $H_2SO_4$ (25 mL), water (3×) and saturated NaCl, dried over anhydrous sodium sulfate and evaporated to an oil. Recrystallization from chloroform-ether gave product that was homogeneous by thin layer chromatography (9:1 chloroform/methanol on Bakerflex silica, Rf=0.44). Yield of tBOC-(O-Bz)-Tyr-Gly-($\epsilon$-$NO_2$)-Arg-ck was 0.93 g (29%).

Tyr-Gly-Arg-ck.2HCl tBOC-(O-Bz)-Tyr-Gly-($\epsilon$-$NO_2$)-Arg-ck (610 mg, 1.0 mmole) was treated with liquified HF for 30 minutes at room temperature. The HF was removed in vacuo and the dried solid was taken up in 1.0 mM HCl and lyophilized. The product was chromatographed on SEPHADEX LH-20 gel in methanol (1×30 cm). The eluted product was collected by evaporation of the solvent in vacuo and recrystallized from methanol/ether. Yield was 319 mg (54%).

Biotinyl-$\epsilon$-aminocaproyl-L-tyrosylglycyl-L-arginine chloromethyl ketone (BioCap-YGRck)

tBOC-(O-Bz)-Tyr-Gly-($\epsilon$-$NO_2$)-Arg-ck (132 mg, 0.20 mmole) was dissolved in saturated HCl/methanol (10 mL) and stirred 10 minutes. The solvent was removed in vacuo and replaced with a second aliquot of the HCl/methanol (10 mL). After 20 minutes, the solvent was removed and ether (50 mL) was added. The solvent was decanted from the precipitated product and the solid was dried in vacuo overnight over KOH pellets.

The residue was dissolved in DMF (1.0 mL) and added to a solution of N-hydroxysuccinyl biotinyl-$\epsilon$-aminocaproate (91 mg, 0.20 mmoles). To this was added $KHCO_3$ (40 mg, 0.40 mmole) in water (0.50 mL). The reaction was allowed to run at 22° C. for 30 minutes then treated with methanolic HCl (5 mL) and ether (50 mL). Two phases were formed. The ether (upper) phase was removed and the lower phase was applied directly to a SEPHADEX LH-20 column (1×20 cm) and eluted with methanol. A single peak was observed by $A_{280}$. This was homogeneous by thin layer chromatography (5:1 chloroform:methanol, $R_f$=0.21). The product was precipitated with ether and collected by filtration. Yield was 69 mg (35%) of the blocked, biotinylated peptide [BioCap-(O-Bz)-Tyr-Gly-($\epsilon$-$NO_2$)-Arg-ck].

The above product (65 mg, 66 mole) was reacted with liquid hydrogen fluoride in a Biosearch HF cleavage reactor. After 30 minutes, the HF was evaporated under vacuum and the dark residue was dried overnight in vacuo over KOH (aspirator vacuum). The residue was treated with 1.0 mM HCl and filtered. The filtrate was lyophilized to an off-white solid which was taken up in methanol (0.5 mL) and chromatographed on SEPHADEX LH-20 gel (1×20 cm) in methanol. Elution gave a single major peak ($A_{280}$) which was Sakaguchi positive and inhibited the reaction of bovine factor Xa with S2222. The pooled peak was evaporated to a solid which was taken up in 1 mM HCl and lyophilized. Yield was 50.2 mg (87%). The solid was taken up in 10 mM HCl and frozen. Final concentration was 13 mM.

Coupling of Fluorophore to Peptide Chloromethyl Ketone

A. Sulfonyl Chloride Method

6-Dimethylaminonapthalene-2-sulfonyl-D-phenylalanyl-L-prolyl-L-arginine chloromethyl ketone hydrochloride [2,6-dansyl-FPRck.HCl]

FPRck.2HCl (Calbiochem) (5.0 mg, 9.5 moles) was dissolved in methanol (1.0 mL) and treated with 2,6-dansyl chloride (Molecular Probes) (2.6 mg, 9.5 $\mu$moles) in DMF (1.0 mL). The solution was mixed and treated with 4-methylmorpholine (20 $\mu$L, 16 $\mu$moles). After 20 minutes at 25° C., the reaction was stopped by addition of 1.0 M HCl (100 μL) and the mixture was applied directly to a SEPHADEX LH-20 column (1×30 cm, in methanol). The elution was followed by fluorescence, $A_{280}$, Sakaguchi stain and thin layer chromatography. The product appeared as a single fluorescent, Sakaguchi positive spot $R_f$=0.14 (2:1 chloroform:methanol on Bakerflex silica gel). The pooled sample was evaporated to an oil and taken up in 1.0 mM HCl. This solution rapidly blocked the reaction of thrombin with synthetic substrate (S2238) and produced fluorescent protein (see labeling procedure below). The solution was lyophilized to an oil which was taken up in 10.0 mM HCl (3.8 mL) and frozen. Final concentration (determined by $A_{360}$) was 1.0 mM. Yield was 3.8 μmoles or 40%.

B. N-Hydroxysuccinimide Ester Method 5 (and 6) Carboxylfluoresceinyl-L-glutamylglycyl-L-arginine chloromethyl ketone hydrochloride [Fl-EGRck].

L-Glutamylglycyl-L-arginine chloromethyl ketone dihydrochloride [16] (13.0 mg, 28 moles) in water (150 μL) was treated in rapid succession with 5(and 6) carboxylfluorescein N-hydroxysuccinimide ester (15.0 mg, 32 moles) in DMF (300 μL) and 1.00 MKHCO$_3$ (50 μL, 50 μmoles). After 10 minutes, 0.10 M HCl (400 μL) was added, and the mixture was applied directly to an LH-20 Sephadex column (1×30 cm in methanol). Elution with methanol gave a single fluorescent band that was homogeneous and Sakaguchi positive. The band was pooled and the solvent removed in vacuo. The residue was taken up in 1.0 mM HCl and lyphilized to an oil which was taken up in 10 mM HCl (5.2 mL) and stored frozen. The concentration (by $A_{490}$) was 1.95 mM. The total yield was 10 μmoles or 36%.

Rate of Hydrolysis of Chloromethyl Ketone

An 0.50 mg/mL solution of bovine factor Xa was prepared and assayed using the S2222 method. A series of tubes containing 50 μL (0.55 nmole) aliquots of this solution were prepared. Fluoresceinyl-EGRck was diluted to 55 μM with Hepes/saline pH=7.4 and 10 μL was added immediately to one of the 50 μL factor Xa aliquots. After incubation for one minute at 20° C., the remaining fctor Xa activity was determined using S2222. Similarly, aliquots of partially hydrolyzed chloromethyl ketone were assayed for remaining inhibitor activity over a four hour period and again at 24 hours. A similar experiment was carried out using human thrombin and 2,6-dansyl-FPRck.

Reaction of Fluoresceinyl-EGRck with bovine factor Xa

Bovine factor Xa (1.0 mg, 22.1 μmoles) in 2.0 mL Hepes/saline pH=7.40 was incubated to 22° C. and tested for reaction with S2222. Fl-EGRck (1.95 mM in 10 mM HCl) was added in aliquots and allowed to react 10 minutes. The residual factor Xa activity was then measured using the S2222 assay.

Preparation of "Blocked" Zymogens

Human factor X (0.5 mg, 1.0 mg/ml, [22 μM] in Hepes/saline pH 7.4) was treated 2,6-Dansyl-EGRck (100 μM final concentration) for 2 hours at room temperature. A second aliquot of inhibitor was added and the reaction was continued overnight. The reaction mixture was applied directly to a SEPHADEX G-25 column (1×20 cm) and eluted with Hepes/saline. The final factor X concentration was 300 ηg/ml.

Human factor VII (0.20 mg, 0.24 mg/mL, 5.0 μM in Hepes/saline) containing 5–10% factor VIIa (by gel analysis) was treated with BioCap-YGRck (final concentration 200 μM) for 2 hours after which a second equal aliquot of BioCap-YGRck was added and allowed to react overnight. The reaction mixture was applied directly to a Sephadex G-25 column (1×30 cm) and eluted with Hepes/saline buffer. The eluate was then stirred for 20 minutes with 0.25 g (88 units) of avidin-acrylic resin (Sigma). The resin was then removed by centrifugation and the supernatant was concentrated in a Centricon 10 to a final concentration of 100 μg/mL. Gel electrophoresis indicated no factor VIIa remained in a preparation.

Chromogenic Assays

Factor Xa: In a one mL cuvette, 22.5 μM S2222 in Hepes/saline pH=7.4 was treated with 1–10 μL of the factor Xa preparation. The mixture was stirred briefly and the absorbance at 405 nm followed in a Cary 219 UV/visible spectrophotometer. The rate was taken for the initial linear phase. Similar methods were used for thrombin (S2238), plasmin (S2251) and tPA (S2238). Hemker, H. C. (1983) in *Handbook of Synthetic Substrates: For the Coagulation and Fibrinolytic Systems.* Martinus Nijhogg Publishers, Boston.

Factor VII: The coupled assay of Nemerson (Nemerson, Y. & Esnouf, M. P. (1973) *Proc. Natl. Acad. Sci. U.S.A.* 70:310–314) was used. Stock solutions of factor X (500 ng/mL), tissue factor (12 ng/mL/lipid (PCPS, 100 μM)) (or thromboplastin) and CaCl$_2$ (20 mM) were mixed in equal volume, incubated for 30 seconds at 37° C. and treated with an aliquot of the first three solutions. The reactions were incubated five minutes, after which aliquots were assayed using the factor Xa/S2222 method described above.

Modifications of this assay were used to determine the level of tissue factor activity and for determining factor X activation in complete or deficient catalytic complexes. Where low levels of factor Xa activity was expected, considerably longer incubation times were used. In the deficient complexes, omitted factor VII or factor X was replaced by Hepes/saline; omitted tissue factor was replaced by phospholipid (PCPS 100 μM).

Avidin-Biotinylated Protein Interactions

To determine the availability of biotin on proteases reacted with biotinylated chloromethyl ketone, the treated protein was passed through Sephadex G-25 to remove unattached probe, then reacted with avidin-fluorescein (Sigma). The fluorescence of the fluorescein was enhanced 75% on binding of biotin to the avidin (both emission and excitation). Use of a standard curve developed with free biotin of known concentration allowed quantitation of the biotin content of the sample. Alternatively, samples were separated by gel electrophoresis and blotted to nitrocellulose in tris/glycine/methanol transfer buffer. After washing with Tris (20 mM)/saline pH=7.4 (TBS) and blocking the nitrocellulose with Tween/TBS, the blot was developed with avidin-biotin-peroxidase and visualized with 4-chloronaphthylamine.

Reaction of Human Factor VII and VIIa with $^3$H-DFP

Human factor VII (49 ug in 100 uL Hepes/saline, 10 μmolar) containing 10% (by gel analysis) factor VIIa was reacted with $^3$H-DFP (10 mM, 0.44 Ci/mmole) for 4 hours. The sample was then separated by SDS PAGE and stained with Coomassie Brilliant Blue. The bands corresponding to factors VII and VIIa were removed and dissolved in 30% hydrogen peroxide at 90° C., dispersed in AGUASOL scintillation medium and counted on a Beckman LS-3133P counter.

Results

The chemical properties and spectral characteristic of the fluorescently labeled chloromethyl ketones are shown in Table II.

TABLE II

| Product | Method/Yield | Rf (3:1) | Absorbance max$^{(nM)/(1/M)}$ | Emission max$^{(nM)}$ |
|---|---|---|---|---|
| 1,5-Dansyl-EGRck | SO$_2$-Cl/52% | 0.39 | 320/4200 | 520 |
| 2,5-Dansyl-EGRCk | SO$_2$-Cl/32% | 0.46 | 370/not done | 475 |
| 2,6-Dansyl-EGRck | SO$_2$-Cl/45% | 0.40 | 359/5700 | 430 |
| Fluorescein-EGRck | -ONSu/36% | 0.30 | 490/73000 | 525 |
| Rhodamine-X-EGRck | -ONSu/25% | 0.25 | 560/85000 | 590 |
| Lissamine-Rhodamine-EGRck | -SO$_2$-Cl/24% | 0.18 | 510/71000 | 590 |
| 6-Pyrene-EGRck | -SO$_2$-Cl/52% | 0.52 | 349/not done | 398 |
| 1,5-Dansyl-FPRck | -SO$_2$-Cl/62% | 0.71 | 320/4200 | 510 |
| 2,6-Dansyl-FPRck | -SO$_2$-Cl/40% | 0.62 | 360/5700 | 430 |
| Fluorescein-FPRck | -ONSu/32% | 0.14 | 490/73000 | 525 |
| Lissamine-Rhodamine-FPRck | -SO$_2$-Cl/50% | 0.12 | 570/71000 | 590 |
| 1,5-Dansyl-TGRck | -SO$_2$-Cl/40% | 0.30 | 320/4200 | 530 |

All were free of unlabeled peptide and free fluorophore and appeared stable on long term storage in 10 mM at −20° C. Contamination by small quantities of hydroxy-methyl ketone could not be ruled out, since the methods used for analysis could be expected to produce small amounts of hydrolysis. The generally high reactivity of the preparations toward proteases indicates that the chloromethyl ketone groups are substantially unhydrolyzed. Chloromethyl ketones which are hydrolyzed by treatment with strong base lose their ability to inhibit proteases. We have noted a tendency for dansyl derivatives to lose fluorescence intensity on standing at room temperature for long periods, even if protected from light. The compounds do, however, retain their ability to inhibit proteases. All of the inhibitors are sensitive to photo-bleaching and were protected from light as much as possible.

To determine the range of activity of the various fluorophore-peptide combinations, proteases and their corresponding zymogens were reacted with large excesses of each reagent. In all cases, the level of reaction was monitored by gel electrophoresis. Fluorescent bands were photographed and marked prior to staining. In all cases, only the active enzymes are able to incorporate label, and only the polypeptide chain known to contain the active site histidine was labeled. All of the proteases tested (factors IIa, VIIa, IXa, Xa, APC, plasmin, tPA (one and two chain) and urokinase) react with [F]-FPRck, [F]-EGRck, and [F]-YGRck ([F]=any fluorescent probe). The reaction rates of urokinase with FPRck derivatives were relatively poor, but all other combinations tested gave essentially quantitative label incorporation at molar excesses of chloromethyl ketone below 5:1. In contrast, none of the zymogen forms could be induced to incorporate label, even at molar ratios in excess of 50:1. When small amounts of label was observed to incorporate into zymogen preparations, gel analysis of the product showed this to be due to traces of activated protease which contaminated the (zymogen) preparation.

The incorporation of label could be monitored directly in those cases where a chromogenic substrate assay was available. In these reactions each aliquot of inhibitor was allowed to react until the rate of incorporation was very small before a subsequent aliquot was added. The slow hydrolysis rate of the chloromethyl ketone precluded waiting until all previously added inhibitor was consumed. Addition was continued until only baseline hydrolysis of the chromogenic substrate could be observed. For a given protease, the total amount of inhibitor required depended both on its structure and on the rate of addition. When [F]-EGRck derivatives were used to block the factor Xa-S2222 reaction, 2–5 molar equivalents were required to block activity. [F]-FPRck and [F]-YGRck derivatives were generally more efficient in inhibition of both factor IIa and factor Xa, typically giving complete inhibition with two or fewer molar equivalents. An alternative method of following the rate of inhibition was to add enzyme to a solution containing both inhibitor and chromogenic substrate. The rate of hydrolysis could be observed to fall off rapidly. However, interpretation of these results is complicated by the competing reactions of chloromethyl ketone hydrolysis and by the relatively rapid depletion of substrate by the still active enzyme.

For enzymes such as factor VIIa, in which the assay procedures involve the coupling of the initial proteolytic event to a subsequent chromogenic step, direct use of the assay to follow factor VIIa (or VII) reaction with chloromethyl ketone was not possible since residual inhibitor reacts rapidly with the enzyme produced (factor Xa), thus interfering with the assay. Completely activated human factor VIIa was reacted with fluoresceinyl-FPRck (1.0 equivalent) and assayed after 20 minutes. The enzyme was inhibited 38% in its ability to generate factor Xa activity. In other cases, reactivity was determined only qualitatively by the incorporation of label into enzyme and electrophoretic separation. In these instances, quantitation of rate was not attempted.

The only combination of active protease and chloromethyl ketone which failed to incorporate substantial fluorescence was two-chain urokinase reacted with FPRck derivatives. This result could be verified by the ability of urokinase to convert plasminogen to plasmin in the presence of lissamine-rhodamine-FPRck.

Direct quantitation of fluorophore-protein ratios in the isolated labeled proteins by absorbance measurements generally gave values close to 1:1, but these measurements are complicated by changes in fluorescence intensity which occur upon binding to protein and by significant levels of fluorescence energy transfer within some of the systems. Table III gives the apparent fluorophore/protein ratios for proteins which were isolated free of non-bound inhibitor.

TABLE III

Quantitation of Fluorophore: Fluorophore-Protein Ratios by Absorbance Of Protein Chloromethyl Ketone

| | | Fluorophore/Protein (mole/mole) |
|---|---|---|
| human Xa | Fluoresceinyl-EGRCk | 1.06 |
| bovine Xa | Fluoresceinyl-EGRCk | 1.02 |
| human Xa | Fluoresceinyl-YPRck | 0.98 |
| human Xa | Rhodamine-X-EGRck | 0.92 |
| human Xa | 2,6-Dansyl-EGRck | 1.06 |
| human IIa | Fluoresceinyl-YPRck | 0.95 |
| human VIIa | Fluoresceinyl-YPRck | 0.91 |

(Protein concentrations were determined from $A_{280}$, corrected for the fluorophore absorbance were indicated. The fluorophore concentration was determined at the absorbance maximum of the particular probe.)

Hydrolysis Rates

Hydrolysis of chloromethyl ketones to the corresponding hydroxymethyl compounds, while significant, is not so rapid at physiological pH as to reliably remove inhibitory activity. As measured by the ability to inhibit activity toward chromogenic substrates, the apparent halflife of chloromethyl ketone in Hepes/salin pH=7.4 at 20° C. is two to five hours, and significant (5–20%) of the inhibitory activity remains after 24 hours. At 37° C., the reaction is somewhat more rapid, but 2–5% activity remains after six hours. The rate of hydrolysis is somewhat faster with EGRck derivatives than with FPRck. Increasing the pH greatly enhances the hydrolysis rate. Five minutes at pH=11.0 (1.0 mM NaOH) results in complete loss of inhibitory activity, suggesting complete hydrolysis.

Fluorescence Properties of the Probes and Probe-Protein Adducts

The fluorescence behavior of the probes is generally not greatly effected by the nature of the peptide or chloromethyl ketone to which it is attached. However, more dramatic changes can occur with protein incorporation. In incorporated probes, wavelength shifts in excitation and emission maxima (relative to the unattached inhibitor) are generally small, typically from 0–5 nM. Some increase generally occurs in excitation at 280 nM. This is attributable to energy transfer between the protein and the probe. The increase is especially pronounced when the probe has an excitation band in the 320–400 nM range. Otherwise, intensity changes in excitation and emission bands are dependent both on the probe and the protein used, and may also be observed on binding of the protease to other components of the proteolytic complex.

Removal of Active Enzymes

The biotinylated chloromethyl ketone, Biotinyl-ε-aminocaproyl-YGRck provides for the facile removal of traces of activate protease from samples. As with the fluorescent probes, only the active proteases react to incorporate the biotinylated peptide. The biotin is when available for binding to avidin, but only on the activated forms. This allows the rapid removal of the blocked protease by reaction with avidin linked to a solid matrix. While complete inhibition of protease activity can be obtained with a variety of active site blocking reagents, physical removal of traces of the protease from zymogen preparations has often proven difficult. This is especially true when the activation occurs with no change in molecular size. This method allows for a simple removal of contaminants and is particularly useful in preparing reagents for detection of small amounts of activation and other applications where traces of protease is undesirable.

Mixtures of human factors VII and VIIa (5–15% VIIa) were reacted with BioCap-YGRck, using five fold excess of chloromethyl ketone (based on total protein). The product was gel filtered to remove excess inhibitor and reacted with avidin linked to a polyacrylate matrix. Gel analysis of the supernant indicated no contamination with factor VIIa. Identical results were obtained when a solution of bovine factor X, doped with 10% (w/w) factor Xa was treated by the same protocol.

The spacing provided by the ε-amino caproyl group is essential for this reaction. When biotin was coupled directly to a peptide chloromethyl ketone, reaction with protease (factors IIa and Xa) proceeded normally, as assayed by chromogenic substrate. However, no binding of avidin could be detected using avidin-acrylic, fluorescein-avidin, or avidin-peroxidase blotting. With the spacer, avidin reacts readily, using any of the above detection methods. The gel filtration step greatly reduces the amount of avidin consumed.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method of detecting or quantifying a catalytically-active form of a particular serine protease in a biological fluid, comprising the steps of:
    (a) incubating with the biological fluid:
        (i) a biotinylated peptidyl halomethyl ketone specific for catalytically-active forms of serine proteases and does not bind the inactive forms, under conditions sufficient for the biotinylated peptidyl halomethyl ketone to be incorporated covalently into the serine proteases, the biotinylated peptidyl halomethyl ketone comprising a peptidyl halomethyl ketone linked to biotin through a spacer group sufficient to make the biotin available for avidin binding after covalent incorporation of the biotinylated peptidyl halomethyl ketone into a serine protease; and
        (ii) an antibody specific for the particular serine protease under conditions which allow the antibody to bind the serine protease; and
    (b) determining the amount of serine protease bound by both the peptidyl halomethyl ketone and the antibody as indicative of the presence or amount of the catalytically-active form of the particular serine protease in the biological fluid.

2. A method of claim 1, wherein the serine protease quantified is selected from the group consisting of tissue plasminogen activator, factor VIIa, factor IIa, factor IXa, factor Xa, plasmin, and activated protein C.

3. A method of determining the amount of a catalytically-active form of a particular serine protease in a biological fluid, comprising the steps of:
    (a) incubating a biotinylated peptidyl chloromethyl ketone specific for the active catalytic site of serine proteases and does not bind the inactive forms with the biological fluid under conditions sufficient for the biotinylated peptidyl chloromethyl ketone to be incorporated covalently into the site, the biotinylated peptidyl chloromethyl ketone comprising a peptidyl chloromethyl ketone linked to biotin through a spacer group sufficient to make the biotin available for avidin binding after covalent incorporation of the biotinylated peptidyl chloromethyl ketone into a serine protease;
    (b) contacting the biological fluid with an immunoadsorbent which contains an antibody specific for the particular serine protease under conditions which allow the serine protease to be adsorbed to the immunoadsorbent;
    (c) separating the immunoadsorbent and the biological fluid;
    (d) contacting the immunoadsorbent with an avidin-bound enzyme; and
    (e) determining the amount of enzymatic activity associated with the immunoadsorbent as indicative of the amount of the catalytically-active form of the particular serine protease in the biological fluid.

4. A method of claim 3, wherein the serine protease quantified is selected from the group consisting of tissue plasminogen activator, urokinase, factor VIIa, factor IIa, factor IXa, factor Xa, plasmin, and activated protein C.

5. A method of claim 3, wherein the biotinylated peptidyl chloromethyl ketone has the formula:

$$\text{biotin}-S-A^3-A^2-A^1-CH_2Cl$$

wherein:
    S is the spacer linking the biotin to $A^3$;
    $A^1$ is an amino acid residue which provides specificity for the S1 subsite of the catalytic site of serine proteases; and $A^2$ and $A^3$ are amino acid residues.

6. A method of claim 5, wherein $A^1$ is arginyl, lysyl or homoarginyl.

7. A method of claim 5, wherein $A^3$ is an aromatic amino acid residue.

8. A method of claim 7, wherein $A^3$ is phenylalanyl, tryptophenyl, tyrosyl or histidyl.

9. A method of claim 5, S is a linker of the formula:

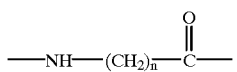

wherein n is 3–8.

10. A method of claim 3, wherein the biotinylated peptidyl chloromethyl ketone has the formula:

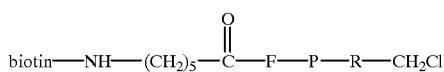

wherein F is phenylalanyl; P is prolyl; and R is arginyl.

11. A method of claim 3, wherein the biotinylated peptidyl chloromethyl ketone has the formula:

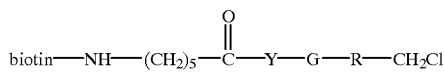

wherein Y is tyrosyl; G is glycyl; and R is arginyl.

12. A method of claim 7, wherein the enzyme is horseradish peroxidase.

13. A method of determining the amount of a catalytically-active form of a particular serine protease in a biological fluid, comprising the steps of:
   (a) incubating a biotinylated peptidyl chloromethyl ketone specific for the active site of serine proteases, with the biological fluid under conditions sufficient for the biotinylated peptidyl chloromethyl ketone to be incorporated into the site, the biotinylated peptidyl chloromethyl ketone comprising a peptidyl chloromethyl ketone linked to biotin through a spacer group sufficient to make the biotin available for avidin binding after covalent incorporation of the biotinylated peptidyl chloromethyl ketone into a serine protease;
   (b) contacting the biological fluid with a solid phase adsorbent containing avidin under conditions which allow serine proteases which have incorporated the biotinylated peptidyl chloromethyl ketone to be adsorbed to the adsorbent;
   (c) separating the adsorbent and the biological fluid;
   (d) contacting the adsorbent with a labeled antibody specific for the particular serine protease to be determined under conditions which allow the antibody to bind the serine protease; and
   (e) determining the amount of label associated with the adsorbent as indicative of the amount of the catalytically-active form of the particular serine protease in the biological fluid.

14. A method of claim 13, wherein the serine protease quantified is selected from the group consisting of tissue plasminogen activator, factor VIIa, factor IIa, factor IXa, factor Xa, plasmin, and protein C.

15. A method of claim 13, wherein the biotinylated peptidyl chloromethyl ketone has the formula;

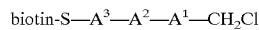

wherein:
   S is the spacer linking biotin to $A^3$;
   $A^1$ is an amino acid residue which provides specificity for the S1 subsite of the catalytic site of serine proteases; and
   $A^2$ and $A^3$ are amino acid residues.

16. A method of claim 15, wherein $A^1$ is arginyl, lysyl or homoarginyl.

17. A method of claim 15, wherein $A^3$ is an aromatic amino acid residue.

18. A method of claim 17, wherein $A^3$ is phenylalanyl, tryptophenyl, tyrosyl or histidyl.

19. A method of claim 15, S is a linker of the formula:

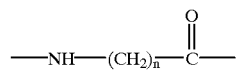

wherein n is 3–8.

20. A method of claim 15, wherein the biotinylated peptidyl chloromethyl ketone has the formula:

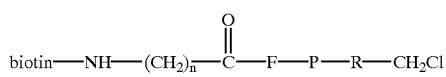

wherein F is phenylalanyl; P is prolyl; R is arginyl; and n is 3–8.

21. A method of claim 15, wherein the biotinylated peptidyl chloromethyl ketone has the formula:

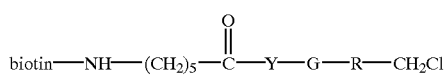

wherein Y is tyrosyl; G is glycyl; and R is arginyl.

22. A method of claim 13, wherein the antibody is labeled with an enzyme.

23. A kit for performing an assay for the catalytically-active form of a particular serine protease, comprising:
   (a) a biotinylated chloromethyl ketone specific for catalytically-active serine proteases, the biotinylated peptidyl chloromethyl ketone comprising a peptidyl chloromethyl ketone linked to biotin through a spacer group sufficient to make the biotin available for avidin binding after covalent incorporation of the biotinylated peptidyl chloromethyl ketone into a serine protease;
   (b) an avidin-coated solid phase adsorbent; and
   (c) labeled antibody specific for the particular serine protease to be determined.

24. A kit of claim 23, wherein the biotinylated chloromethyl ketone has the formula:

wherein:
   S is the spacer linking biotin to $A^3$;
   $A^1$ is an amino acid residue which provides specificity for the S1 subsite of the catalytic site of serine proteases; and
   $A^2$ and $A^3$ are amino acid residues.

25. A kit of claim 24, wherein $A^1$ is arginyl, lysyl or homoarginyl; $A^3$ is phenylalanyl, tryptophenyl, tyrosyl or histidyl; S is a linker of the formula:

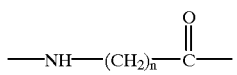

wherein n is 5–8.

26. A kit for performing an assay for the catalytically-active form of a particular serine protease, comprising:
(a) biotinylated peptidyl chloromethyl ketone specific for catalytically-active serine proteases, the biotinylated peptidyl chloromethyl ketone comprising a peptidyl chloromethyl ketone linked to biotin through a spacer group sufficient to make the biotin available for avidin binding after covalent incorporation of the biotinylated peptidyl chloromethyl ketone into a serine protease;
(b) avidin-bound label; and
(c) antibody-coated immunoadsorbent, the antibody being specific for the particular serine protease to be determined.

27. A kit of claim 26, wherein the biotinylated peptidyl chloromethyl ketone has the formula:

wherein:
S is the spacer linking biotin to $A^3$;
$A^1$ is an amino acid residue which provides specificity for the S1 subsite of the catalytic site of serine proteases; and
$A^2$ and $A^3$ are amino acid residues.

28. A kit of claim 27, wherein $A^1$ is arginyl, lysyl, homoarginyl, phenylalanyl or threonyl; $A^3$ is phenylalanyl, tryptophenyl, tyrosyl or seryl and S is a linker of the formula:

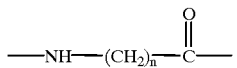

wherein n is 3–8.

29. A biotinylated peptidyl chloromethyl ketone having the formula:

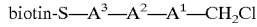

wherein:
S is the spacer linking biotin to $A^3$;
$A^1$ is an amino acid residue which provides specificity for the S1 subsite of the catalytic site of serine proteases;
$A^2$ and $A^3$ are amino acid residues; and further wherein the spacer group is sufficient to make the biotin available for avidin binding after covalent incorporation of the biotinylated peptidyl chloromethyl ketone into a serine protease.

30. A biotinylated chloromethyl ketone of claim 29, wherein $A^1$ is arginyl, lysyl or homoarginyl.

31. A biotinylated chloromethyl ketone of claim 29, wherein $A^3$ is an aromatic amino acid residue.

32. A biotinylated chloromethyl ketone of claim 31, wherein $A^3$ is phenylalanyl, tryptophenyl, tyrosyl or histidyl.

33. A biotinylated chloromethyl ketone of claim 29, S is a linker of the formula:

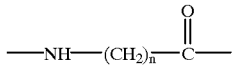

wherein n is 3–8.

34. A biotinylated peptidyl chloromethyl ketone having the formula:

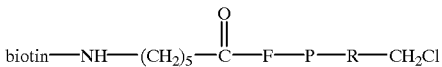

wherein F is phenylalanyl; P is prolyl; and R is arginyl.

35. A biotinylated peptidyl chloromethyl ketone having the formula:

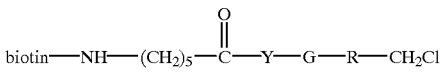

wherein Y is tyrosyl; G is glycyl; and R is arginyl.

36. A method of removing catalytically-active serine proteases from a biological fluid, comprising the steps of:
(a) incubating a biotinylated chloromethyl ketone specific for the active site of serine proteases, with the biological fluid under conditions sufficient for the biotinylated chloromethyl ketone to be incorporated into the site, the biotinylated peptidyl chloromethyl ketone comprising a peptidyl chloromethyl ketone linked to biotin through a spacer group sufficient to make the biotin available for avidin binding after covalent incorporation of the biotinylated peptidyl chloromethyl ketone into a serine protease;
(b) contacting the biological fluid with a solid phase adsorbent containing avidin under conditions which allow serine proteases which have incorporated the biotinylated chloromethyl ketone to be adsorbed to the adsorbent; and
(c) separating the adsorbent and the biological fluid.

* * * * *